United States Patent [19]
Opper et al.

[11] Patent Number: 6,008,023
[45] Date of Patent: Dec. 28, 1999

[54] **CYTOPLASMIC EXPRESSION OF ANTIBODIES, ANTIBODY FRAGMENTS AND ANTIBODY FRAGMENT FUSION PROTEINS IN *E. COLI***

[75] Inventors: Martin Opper; Klaus Bosslet; Joerg Czech, all of Marburg, Germany

[73] Assignee: Hoechst Marion Roussel Deutschland GmbH, Frankfurt am Main, Germany

[21] Appl. No.: 08/630,820

[22] Filed: Apr. 10, 1996

[30] Foreign Application Priority Data

Apr. 11, 1996 [DE] Germany .................. 195 13 676

[51] Int. Cl.$^6$ .................. C07H 21/02; C07H 21/04; C12N 15/13; C12N 15/03
[52] U.S. Cl. .................. 435/69.7; 435/69.6; 435/170; 435/183; 435/189; 435/471; 435/252.33; 435/849; 530/387.3; 424/134.1; 424/801; 536/23.2; 536/23.4; 536/23.53
[58] Field of Search .................. 435/1, 72.3, 344, 435/69.6, 71.2, 471, 170, 183, 189, 252.33, 849, 69.7; 530/387.3, 387.7; 536/23.4, 23.53, 23.2; 424/134.1, 801

[56] References Cited

U.S. PATENT DOCUMENTS 5,648,237 7/1997 Carter et al. .................. 435/69.1

FOREIGN PATENT DOCUMENTS 0 623 352 A1 4/1994 European Pat. Off. .

OTHER PUBLICATIONS

Gillies et al Human Antibodies Hybridomas vol. 1(1) 47–54, 1990.
Axelsson Acta Chemica Scandanavica Series B vol. 39(1) 69–77, 1985.
Paulus et al Behring inst Mitt No. 78 118–132, 1985.
Burgess et al Journal of Cell Biology vol. 111 2129–2138, Nov. 1990.
Lazar et al Molecular and Cellular Biology vol. 8 No. 3 1247–1252, Mar. 1988.
Schwartz et al Proc Natl Acad Sci USA vol. 84 6408–6411, 1987.
Lin et al Biochemistry USA vol. 14 1559–1563, 1975.
Rodrigues et al Cancer Research vol. 55 63–70, Jan. 1995.
Gussow et al., "Humanization of Monoclonal Antibodies" Methods in Enzymology, vol. 203, (1991) pp. 99–121.
Bosslet et al., "Molecular and Functional Characterization of a Fusion Protein Suited for Tumor Specific Prodrug Activation", Br. J. Cancer, vol. 65 (1992), pp. 234–238.
Derman et al., "Mutations that Allow Disulfide Bond Formation in the Cytoplasm of *Escherichia Coli*", Science, vol. 262, (1993) pp. 1744–1747.
Jefferson et al., "B–Glucuronidase from *Escherichia Coli* as a Gene–Fusion Marker", Proc. Natl. Acad. Sci., vol. 83, (1986), pp. 8447–8451.
Ayala et al., "Bacterial Single–Chain Antibody Fragments, Specific for Carcinoembryonic Antigen", BioTechniques, vol. 13, No. 5, (1992), pp. 790–799.
Goshorn et al., "Genetic Construction, Expression, and Characterization of a Single Chain Anti–Carcinoma Antibody Fused to B–Lactamase", Cancer Res., vol. 53, (1993), pp. 2123–2127.
Amann et al., "Tightly Regulated tac Prometer Vectors Useful for the Expressionof Unfused and Fused Proteins in *Escherichia Coli*", Gene, vol. 69, (1983), pp. 301–315.
Bagshawe, "Towards Generating Cytotoxic Agents at Cancer Sites", Br. Jr. Cancer, vol. 60, (1989), pp. 275–281.
Pluckthun et al., "Expression of Functional Antibody Fv and Fb Fragments in *Escherichia Coli*", Methods in Enzymology, vol. 178, (1989), pp. 497–515.

*Primary Examiner*—Julie Reeves
*Attorney, Agent, or Firm*—Foley & Lardner

[57] ABSTRACT

The invention relates to the cytoplasmic expression of antibodies, antibody fragments and antibody fragment fusion molecules in *E. coli*. In particular, antibody fragment fusion molecules having an antibody moiety which is directed against tumors and an enzyme moiety which cleaves a nontoxic prodrug to give the toxic drug can be advantageously prepared in this way while retaining their respective functional properties.

9 Claims, 16 Drawing Sheets

FIG.1a

E.c. β-Gluc for:   5' AAG CTT TCA TTG TTT GCC TCC CTG CTG CTG CGG 3'

E.c. β-Gluc back:  5' TCT AGA CCA TGG TAC GTC CTG TAC AAA CCC CA 3'

FIG.2a

Fab HC for:  5' <u>GAA TTC</u> <u>CAT GGA</u> ACC AGA ACC AGA ACC GAG CTC AAC TCT N2
　　　　　　　　　　　　　　　　　　　　　　　　　　　　　　　link

CTT GTC CAC CTT GGT GTT 3'
　　　　　CH1

Fab HC back: 5' <u>TCT AGA</u> TAA CGA GGG CAA AAA ATG GAG GTC CAA CTG CAG N2b
　　　　　　　　　　　　　　　　　SD　　　　　　　　　　　　　　　　　　　VH

GAG AGC 3'

PCR + Cloning into KS+

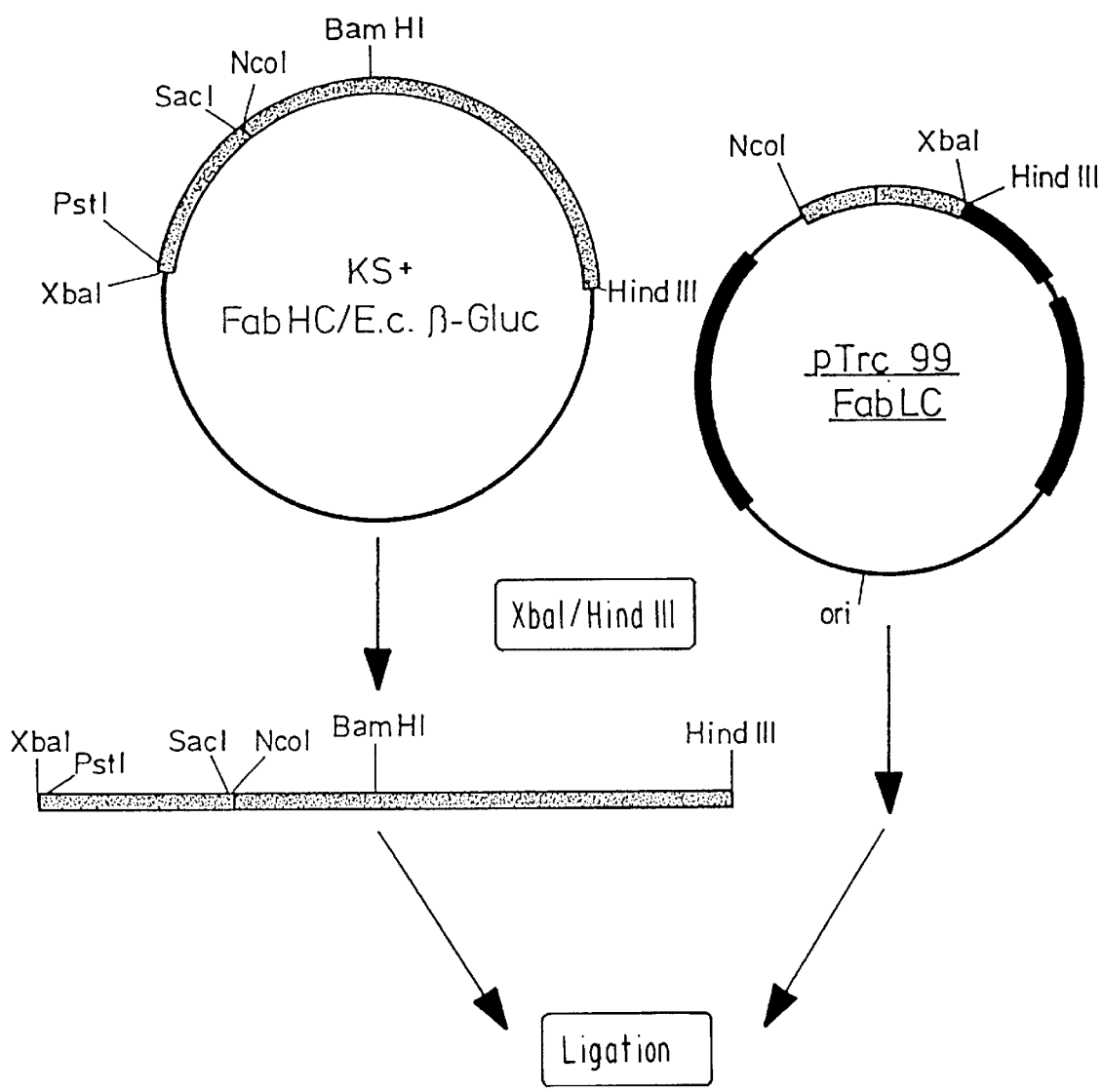
FIG. 4
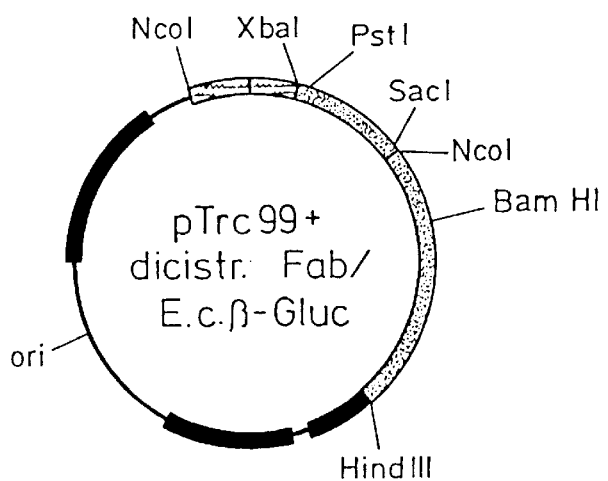

431/26 hum dicistr. Fab/E.c.β-Glucuronidase in pTrc 99

FIG. 5b

```
     NcoI                                                                              N5
  1  CC ATG GAC ATC CAG ATG ACC CAG AGC CCA AGC AGC CTG AGC GCC GTG GGT GAC AGA
   1▸Met Asp Ile Gln Met Thr Gln Ser Pro Ser Ser Leu Ser Ala Val Gly Asp Arg

60  GTG ACC ATC ACC TGT AGT ACC AGT GTA AGT TAC ATG CAC TGG TAC CAG CAG AAG
  20▸Val Thr Ile Thr Cys Ser Thr Ser Val Ser Tyr Met His Trp Tyr Gln Gln Lys

VK
120  CCA GGT AAG GCT CCA AAG CTG CTG ATC TAC AGC ACA TCC AAC CTG GCT TCT GGT GTG CCA
  40▸Pro Gly Lys Ala Pro Lys Leu Leu Ile Tyr Ser Thr Ser Asn Leu Ala Ser Gly Val Pro

180  AGC AGA TTC AGC GGT AGC GGT AGC GGT ACC GAC TTC ACC TTC ACC ATC AGC AGC CTC CAG
  60▸Ser Arg Phe Ser Gly Ser Gly Ser Gly Thr Asp Phe Thr Phe Thr Ile Ser Ser Leu Gln

240  CCA GAG GAC ATC GCC ACC TAC TAC TGC CAT CAG TGG AGT AGT TAT CCC ACG TTC GGC CAA
  80▸Pro Glu Asp Ile Ala Thr Tyr Tyr Cys His Gln Trp Ser Ser Tyr Pro Thr Phe Gly Gln

300  GGG ACC AAG GTG GAA ATC AAA CGT ACT GTG GCT GCA CCA TCT GTC TTC ATC TTC CCG CCA
 100▸Gly Thr Lys Val Glu Ile Lys Arg Thr Val Ala Ala Pro Ser Val Phe Ile Phe Pro Pro.
```

FIG. 5c

```
                                                                    CK
360 TCT GAT GAG CAG TTG AAA TCT GGA ACT GCC TCT GTT GTG TGC CTG AAT AAC TTC TAT
120▶Ser Asp Glu Gln Leu Lys Ser Gly Thr Ala Ser Val Val Cys Leu Asn Asn Phe Tyr

420 CCC AGA GAG GCC AAA GTA CAG TGG AAG GTG GAT AAC GCC CTC CAA TCG GGT AAC TCC CAG
140▶Pro Arg Glu Ala Lys Val Gln Trp Lys Val Asp Asn Ala Leu Gln Ser Gly Asn Ser Gln

480 GAG AGT GTC ACA GAG CAG GAC AGC AAG GAC TAC GAG AGC ACC TAC AGC CTC AGC ACC CTG ACG
160▶Glu Ser Val Thr Glu Gln Asp Ser Lys Asp Tyr Glu Ser Thr Tyr Ser Leu Ser Thr Leu Thr

540 CTG AGC AAA GCA GAC TAC GAG AAG CAC AAA GTC TAC GCC TGC GAA GTC ACC CAT CAG GGC
180▶Leu Ser Lys Ala Asp Tyr Glu Lys His Lys Val Tyr Ala Cys Glu Val Thr His Gln Gly
                                                                              XbaI
600 CTG AGC TCG CCC GTC ACA AAG AGC TTC AAC AGG GGA GAG TGT TAG TCTAGATAACGAGGCAAA
200▶Leu Ser Ser Pro Val Thr Lys Ser Phe Asn Arg Gly Glu Cys ···
         PstI
664 AA ATG GAG GTC CAA CTG CAG GAG AGC GGT CCA GGT CTT GTG AGA CCT AGC CAG ACC CTG
  1▶Met Glu Val Gln Leu Gln Glu Ser Gly Pro Gly Leu Val Arg Pro Ser Gln Thr Leu
```

```
 723  AGC CTG ACC TGC ACC GTG TCT GGC TTC ACC ATC AGC AGT GGT TAT AGC TGG CAC TGG GTG
  20▸ Ser Leu Thr Cys Thr Val Ser Gly Phe Thr Ile Ser Ser Gly Tyr Ser Trp His Trp Val

783  AGA CAG CCA CCT GGA CGA GGT CTT GAG TGG ATT GGA TAC ATA CAG TAC AGT GGT ATC ACT
  40▸ Arg Gln Pro Pro Gly Arg Gly Leu Glu Trp Ile Gly Tyr Ile Gln Tyr Ser Gly Ile Thr

843  AAC TAC AAC CCC TCT CTC AAA AGT AGA GTG ACA ATG CTG GTA GAC ACC AGC AAG AAC CAG
  60▸ Asn Tyr Asn Pro Ser Leu Lys Ser Arg Val Thr Met Leu Val Asp Thr Ser Lys Asn Gln

903  TTC AGC CTG AGA CTC AGC AGC GTG ACA GCC GAC ACC GCG GTC TAT TAT TGT GCA AGA
  80▸ Phe Ser Leu Arg Leu Ser Ser Val Thr Ala Asp Thr Ala Val Tyr Tyr Cys Ala Arg

963  GAA GAC TAT GAT TAC TTC GAT GTC TGG GGT CAA GGG ACC TCG GTC ACA GTC
 100▸ Glu Asp Tyr Asp Tyr Phe Asp Val Trp Gly Gln Gly Thr Ser Val Thr Val

1023  ACA GTC TTC TCA GCT TCC ACC AAG GGC CCA TCG GTC TTC CCC CTG GCG CCC TGC TCC AGG
 120▸ Thr Val Phe Ser Ala Ser Thr Lys Gly Pro Ser Val Phe Pro Leu Ala Pro Cys Ser Arg

1083  AGC ACC TCT GGG GGC ACA GCG GCC CTG GGC TGC CTG GTC AAG GAC TAC TTC CCC GAA CCG
 140▸ Ser Thr Ser Gly Gly Thr Ala Ala Leu Gly Cys Leu Val Lys Asp Tyr Phe Pro Glu Pro
```

```
1143 GTG ACG GTG TCG TGG AAC TCA GGC GCC CTG ACC AGC GGC GTG CAC ACC TTC CCG GCT GTC
 160▶ Val Thr Val Ser Trp Asn Ser Gly Ala Leu Thr Ser Gly Val His Thr Phe Pro Ala Val

1203 CTA CAG TCC TCA GGA CTC TAC TCC CTC AGC AGC GTG GTG ACC GTG CCC TCC AGC AGC TTG
 180▶ Leu Gln Ser Ser Gly Leu Tyr Ser Leu Ser Ser Val Val Thr Val Pro Ser Ser Ser Leu

1263 GGC ACC CAG ACC TAC ACC TGC AAC GTG AAT CAC AAG CCC AGC AAC ACC AAG GTG GAC AAG
 200▶ Gly Thr Gln Thr Tyr Thr Cys Asn Val Asn His Lys Pro Ser Asn Thr Lys Val Asp Lys
                              link              NcoI 1323 AGA GTT GAG CTC GGT TCT GGT TCC ATG GTA CGT CCT GTA GAA ACC CCA ACC CCT
 220▶ Arg Val Glu Leu Gly Ser Gly Ser Met Val Arg Pro Val Glu Thr Pro Thr Arg
          SacI 1383 GAA ATC AAA AAA CTC GAC GGC CTG TGG GCA TTC AGT CTG GAT CGC GAA AAC TGT GGA ATT
 240▶ Glu Ile Lys Lys Leu Asp Gly Leu Trp Ala Phe Ser Leu Asp Arg Glu Asn Cys Gly Ile 1443 GAT CAG CGT TGG TGG GAA AGC GCG TTA CAA GAA AGC CGG GCA ATT GCT GTG CCA GGC AGT
 260▶ Asp Gln Arg Trp Trp Glu Ser Ala Leu Gln Glu Ser Arg Ala Ile Ala Val Pro Gly Ser 1503 TTT AAC GAT CAG TTC GCC GAT GCA GAT ATT CGT AAT TAT GCG GGC AAC GTC TGG TAT CAG
 280▶ Phe Asn Asp Gln Phe Ala Asp Ala Asp Ile Arg Asn Tyr Ala Gly Asn Val Trp Tyr Gln
```

E.c. β-Gluc

FIG. 5f

```
1563 CGC GAA GTC TTT ATA CCG AAA GGT TGG GCA GCC CAG CGT ATC GTG CTG CGT TTC GAT GCG
300► Arg Glu Val Phe Ile Pro Lys Gly Trp Ala Gly Gln Arg Ile Val Leu Arg Phe Asp Ala

1623 GTC ACT CAT TAC GGC AAA GTG TGG GTC AAT AAT CAG GAA GTG ATG GAG CAT CAG GGC GGC
320► Val Thr His Tyr Gly Lys Val Trp Val Asn Asn Gln Glu Val Met Glu His Gln Gly Gly

1683 TAT ACG CCA TTT GAA GCC GAT GTC ACG CCG TAT GTT ATT GCC GGG AAA AGT GTA CGT ATC
340► Tyr Thr Pro Phe Glu Ala Asp Val Thr Pro Tyr Val Ile Ala Gly Lys Ser Val Arg Ile

BamHI
1743 ACC GTT TGT GTG AAC AAC GAA CTG AAC TGG CAG ACT ATC CCG GGA ATG GTG ATT ACC
360► Thr Val Cys Val Asn Asn Glu Leu Asn Trp Gln Thr Ile Pro Pro Gly Met Val Ile Thr

1803 GAC GAA AAC GGC AAG AAA CAG TCT TAC TTC CAT AAT TTC TTT AAC TAT GCC GGG ATC
380► Asp Glu Asn Gly Lys Lys Gln Ser Tyr Phe His Asn Phe Phe Asn Tyr Ala Gly Ile

1863 CAT CGC AGC GTA ATG CTC TAC ACC ACG CCG AAC ACC TGG GTG GAC GAT ATC ACC GTG GTG
400► His Arg Ser Val Met Leu Tyr Thr Thr Pro Asn Thr Trp Val Asp Asp Ile Thr Val Val

1923 ACG CAT GTC GCG CAA GAC TGT AAC CAC CGG TCT GTT GAC TGG CAG GTG GTG GCC AAT GGT
420► Thr His Val Ala Gln Asp Cys Asn His Arg Ser Val Asp Trp Gln Val Val Ala Asn Gly
```

FIG. 5g

```
1983 GAT GTC AGC GTT GAA CTG CGT GAT GCG GAT CAA CAG GTG GCA ACT GGA CAA GGC ACT
 440▶Asp Val Ser Val Glu Leu Arg Asp Ala Asp Gln Gln Val Ala Thr Gly Gln Gly Thr

2043 AGC GGG ACT TTG CAA GTG GTG AAT CCG CAC CTC TGG CAA CCG GGT GAA GGT TAT CTC TAT
 460▶Ser Gly Thr Leu Gln Val Val Asn Pro His Leu Trp Gln Pro Gly Glu Gly Tyr Leu Tyr

2103 GAA CTG TGC GTC ACA GCC AAA AGC CAG ACA GAG TGT GAT ATC TAC CCG CTT CGC GTC GGC
 480▶Glu Leu Cys Val Thr Ala Lys Ser Gln Thr Glu Cys Asp Ile Tyr Pro Leu Arg Val Gly

2163 ATC CGG TCA GTG GCA GTG AAG GCC GAA CAG TTC CTG ATT AAC CAC AAA CCG TTC GAT AAC GTG TAC TTT
 500▶Ile Arg Ser Val Ala Val Lys Gly Glu Gln Phe Leu Ile Asn His Lys Pro Phe Asp Asn Val Tyr Phe

2223 ACT GGC TTT GGT CGT CAT GAA GAT GCG GAC TTA CGT GGC AAA GGA TTC GGC AAC TCC TAC CGT ACC TCG CTG
 520▶Thr Gly Phe Gly Arg His Glu Asp Ala Asp Leu Arg Gly Lys Gly Phe Asp Asn Val Leu

2283 ATG GTG CAC GAC CAC GCA TTA ATG GAC TGG ATT GGG GCC AAC TCC TAC CGT ACC TCG CAT
 540▶Met Val His Asp His Ala Leu Met Asp Trp Ile Gly Ala Asn Ser Tyr Arg Thr Ser His
```

FIG. 5h

```
2343 TAC CCT TAC GCT GAA GAG ATG CTC GAC TGG GCA GAT GAA CAT GGC ATC GTG ATT GAT
 560▶Tyr Pro Tyr Ala Glu Glu Met Leu Asp Trp Ala Asp Glu His Gly Ile Val Ile Asp

2403 GAA ACT GCT GTC GGC TTT AAC CTC TCT TTA GGC ATT GGT TTC GAA GCG GGC AAC AAG
 580▶Glu Thr Ala Val Gly Phe Asn Leu Ser Leu Gly Ile Gly Phe Glu Ala Gly Asn Lys

2463 CCG AAA GAA CTG TAC AGC GAA GAG GCA GTC AAC GGG GAA ACT CAG CAA CGG CAC TTA CAG
 600▶Pro Lys Glu Leu Tyr Ser Glu Glu Ala Val Asn Gly Glu Thr Gln Gln Ala His Leu Gln

2523 GCG ATT AAA GAG CTG ATA GCG CGT GAC AAA AAC CAC CCA AGC GTG GTG ATG TGG AGT ATT
 620▶Ala Ile Lys Glu Leu Ile Ala Arg Asp Lys Asn His Pro Ser Val Val Met Trp Ser Ile

2583 GCC AAC GAA CCG GAT ACC CGT CCG CAA GGT GCA CGG GAA TAT TTC GCG CCA CTG GCG GAA
 640▶Ala Asn Glu Pro Asp Thr Arg Pro Gln Gly Ala Arg Glu Tyr Phe Ala Pro Leu Ala Glu

2643 GCA ACG CGT AAA CTC GAC CCG ACG CGT CCG ATC ACC TGC GTC AAT GTA ATG TTC TGC GAC
 660▶Ala Thr Arg Lys Leu Asp Pro Thr Arg Pro Ile Thr Cys Val Asn Val Met Phe Cys Asp

2703 GCC CAC ACC GAT ACC ATC AGC GAT CTC TTT GAT GTG CTG TGC CTG AAC CGT TAT TAC GGA
 680▶Ala His Thr Asp Thr Ile Ser Asp Leu Phe Asp Val Leu Cys Leu Asn Arg Tyr Tyr Gly

2763 TGG TAT GTC CAA AGC GGC GAT TTG GAA ACG GCA GAG AAG GTA CTG GAA AAA GAA CTT CTG
 700▶Trp Tyr Val Gln Ser Gly Asp Leu Glu Thr Ala Glu Lys Val Leu Glu Lys Glu Leu Leu
```

FIG. 5i

```
2823 GCC TGG CAG GAG AAA CTG CAT CAG CCG ATT ATC ATC ACC GAA TAC GGC GTG GAT ACG TTA
720▶Ala Trp Gln Glu Lys Leu His Gln Pro Ile Ile Ile Thr Glu Tyr Gly Val Asp Thr Leu

2883 GCC GGG CTG CAC TCA ATG TAC ACC GAC ATG TGG AGT GAA GAG TAT CAG TGT GCA TGG CTG
740▶Ala Gly Leu His Ser Met Tyr Thr Asp Met Trp Ser Glu Glu Tyr Gln Cys Ala Trp Leu

2943 GAT ATG TAT CAC CGC GTC TTT GAT CGC GTC AGC GCC ATA TTG CAA GTA TGG AAT
760▶Asp Met Tyr His Arg Val Phe Asp Arg Val Ser Ala Val Gly Glu Gln Val Trp Asn

3003 TTC GCC GAT TTT GCG ACC TCG CAA GGC ATA TTG CGC GTT GGC GGT AAC AAG AAA GGG ATC
780▶Phe Ala Asp Phe Ala Thr Ser Gln Gly Ile Leu Arg Val Gly Gly Asn Lys Lys Gly Ile

3063 TTC ACT CGC GAC CGC AAA CCG AAG TCG GCG GCT TTT CTG CAA AAA CGC TGG ACT GGC
800▶Phe Thr Arg Asp Arg Lys Pro Lys Ser Ala Ala Phe Leu Gln Lys Arg Trp Thr Gly

HindIII
3123 ATG AAC TTC GGT GAA AAA CCG CAG CAG GGA GGC AAA CAA TGA AGCTT
820▶Met Asn Phe Gly Glu Lys Pro Gln Gln Gly Gly Lys Gln ...
```

TSK - 3000 Gel chromatography. Retention time of the fusion protein, 13.4 min.
A: Thyroglobulin 670.000 D
B: Gamma-Globulin 158.000 D
C: Ovalbumin 44.000 D
D: Myoglobulin 17.000 D
E: Vitamin B-12 1.350 D

CYTOPLASMIC EXPRESSION OF ANTIBODIES, ANTIBODY FRAGMENTS AND ANTIBODY FRAGMENT FUSION PROTEINS IN *E. COLI*

BACKGROUND OF THE INVENTION

The expression of functional antibodies and antibody fragments in *E. coli* is known in the prior art, but these methods require the use of signal sequences which direct polypeptide transport into the periplasm. When expression takes place in the *E. coli* periplasm, the expression yields are in the range of a few μg per liter of culture medium (Ayala et al., Bio Techniques 13, pp. 790–799, 1992). In addition, refolding experiments are often required in order to obtain functionally active antibody fragments (such as Fab) or antigen-binding regions (such as a single chain Fv(sFv)). There is a need therefore, to develop improved methods for expressing functionally active antibodies and antibody fragments. The prior art does not teach recombinant production of antibodies or antibody fragments which can be isolated from the cytoplasm in functional form. Such molecules would be useful in the production of therapeutic agents.

Bagshawe describes a method for generating cytotoxic agents that are directed towards cancer sites, termed Antibody Directed Enzyme Prodrug Therapy (ADEPT). Bagshawe, Br. J. Cancer, vol. 60, pp. 275–281, 1989. Using ADEPT, an antibody or antibody fragment that specifically binds to a cancer cell is fused to an enzyme that is capable of converting a non-toxic drug into a toxic drug. Only those cells to which the fusion protein is bound will be killed upon administration of the precursor of the toxic drug.

The β-glucuronidase of *Escherichia coli* has been well characterized biochemically and genetically. The gene (uid A) has been cloned by Jefferson et al. (PNAS vol. 83, pp. 8447–8451, 1986) and employed as a reporter gene for heterologous control regions.

β-Glucuronidase (β-glucuronoside glucuronosohydrolase, E.C. 3.2.1.31) is an acid hydrolase which catalyzes the cleavage of β-glucuronides. As a result of the mammalian glucuronidases having been intensively investigated, a variety of substances are available for histological, spectrophotometric and fluorometric analyses. This enzyme has gained new, additional importance in its use for fusion proteins for targeted tumor therapy. In this connection, human glucuronidase is used in the form of a fusion protein which contains antibodies/antibody fragments or antigen-binding regions (Bosslet et al., Br. J, Cancer, 65, 234–238, 1992). As an alternative to the human enzyme, it is also possible to use the homologous *E. coli* β-glucuronidase. One of the advantages of the *E. coli* β-glucuronidase is that its catalytic activity at physiological pH is significantly higher than that of the human β-glucuronidase.

In the past, it has only been possible to express antibody fragment-enzyme fusion molecules periplasmically in *E. coli*. The enzyme moiety which is used in this context is therefore always composed of periplasmic *E. coli* enzymes such as β-lactamase (Goshorn et al., Canc. Res. 53, 2123–2117, 1993).

An *E. coli* strain which is deficient in thioredoxin reductase (TRR), for example the strain AD 494, is capable of forming disulfide bridges in the cytoplasm and thus enzymes which are naturally secretory, for example alkaline phosphatase, can be expressed intracellularly See Derman et al., Science, 262:1744–1747, 1993. Derman describes the selection and isolation of TRR-deficient *E. coli* mutants.

The prior art does not teach expression of an antibody fragment-enzyme fusion molecule using a cytoplasmic *E. coli* enzyme, such as β-glucuronidase, which is functionally active—i.e., which retains both enzymatic activity and antigen-binding ability of the antibody moiety. As a rule, functionally active expression of most antibodies or antibody fragment molecules requires defined signal sequences for exporting the expressed molecules via the endoplasmic reticulum into the culture medium (animal cells and yeast) or into the periplasm (*E. coli*). It is only in the endoplasmic reticulum or in the periplasm that the necessary oxidative conditions pertain for forming the disulfide bridges which are important for functional activity. In addition, the secretory synthesis route is often crucial for the correct three-dimensional folding of the expressed protein.

SUMMARY OF THE INVENTION

Thus, it is an object of the invention to provide a method for the production of functional antibodies and antibody fragments in *E. coli* in which the antigen-binding polypeptides can be isolated from the cytoplasm without the need for further processing such as protein folding and disulfide bond formation.

It is also an object of the invention to provide a method for the production of fusion polypeptides in *E. coli* comprising antibody or antibody fragment and an enzyme, in which the antibody or antibody fragment and the enzyme retain functionality and in which the functional fusion polypeptide can be isolated from the cytoplasm without the need for further processing such as protein folding and disulfide bond formation.

The invention relates, therefore, to processes for the recombinant expression of antibodies, antibody fragments or antibody fragment fusion molecules containing cytoplasmic mammalian or *E. coli* enzymes as fusion partners using thioredoxin reductase-deficient *E. coli* strains and subsequent isolation of the expression products from the cytoplasm.

The invention relates to the cytoplasmic expression of antibodies, antibody fragments and antibody fragment fusion molecules in *E. coli*. In particular, antibody fragment fusion molecules having an antibody moiety which is directed against tumors and an enzyme moiety which cleaves a nontoxic prodrug to give the toxic drug can be advantageously prepared in this way while retaining their respective functional properties.

Accordingly in one embodiment, the invention provides a method for producing an antibody or antibody fragment comprising:

a) transforming a thioredoxin reductase-deficient *E. coli* strain with a nucleotide molecule encoding said antibody or antibody fragment;

b) culturing said transformed *E. coli* strain to allow for expression of said antibody or antibody fragment; and c) isolating said antibody or antibody fragment from the cytoplasm of said transformed *E. coli*.

In a further embodiment, the invention also provides a method for producing a fusion protein comprising an antibody or antibody fragment and an enzyme, said method comprising:

a) transforming a thioredoxin reductase-deficient *E. coli* strain with a nucleotide molecule encoding said fusion protein;

b) culturing said transformed *E. coli* strain to allow for expression of said fusion polypeptide; and c) isolating said fusion polypeptide from the cytoplasm of said transformed *E. coli*.

In another embodiment, the antibody fragment used in the methods of the invention is selected from the group consisting of an Fab fragment, an Fv fragment, an sFv fragment and an F(ab')$_2$ fragment. The antibody used in the methods of the invention can be a humanized antibody. The invention further provides an embodiment wherein the antibodies used in the method of the invention can be antibodies or antibody fragment binds specifically to tumor cells.

In another embodiment, an enzyme used in the method for making a fusion protein is capable of cleaving a nontoxic prodrug to produce a toxic drug and may be a human cytoplasmic enzyme.

In a further embodiment, the fusion protein produced according to the invention comprises an antibody or antibody fragments that is capable of specifically binding to tumor cells and an enzyme capable of cleaving a nontoxic prodrug to produce a toxic drug.

In a further embodiment, the fusion protein produced according to the invention comprises a humanized antibody and a human cytoplasmic enzyme. In another embodiment, the invention comprises a fusion protein comprising *E. coli* β-glucuronidase.

In another embodiment, the invention provides fusion proteins comprising an antibody or antibody fragment and an enzyme. The invention further provides fusion proteins produced according to the methods of the invention. In a further embodiment, a fusion polypeptide comprising *E. coli* β-glucuronidase and an antibody or antibody fragment is provided.

In a further embodiment, a nucleotide sequence encoding a fusion protein comprising an antibody or antibody fragment and an enzyme is provided. In still a further embodiment, the invention provides a nucleotide sequence encoding a fusion polypeptide comprising *E. coli* β-glucuronidase and an antibody or antibody fragment. In yet another embodiment, a nucleotide sequence encoding the amino acid sequence in FIG. 5 which begins at nucleotide number 666 and ends at nucleotide number 3162 is provided. In a final embodiment, a nucleotide sequence is provided wherein said sequence is the nucleotide sequence in FIG. 5 which beings at nucleotide number 666 and ends at nucleotide number 3165.

BRIEF DESCRIPTION OF THE FIGURES

FIG. 1b illustrates the insertion of the DNA sequence for *E. coil* β-glucuronidase into the vector p bluescript II KS (KS) to produce vector KS/A.c.-β-Gluc. The sequences of the primers (SEQ ID NOS:1–2) used to amplify the β-glucuronidase gene are also shown FIG. 1a.

FIG. 2a shows the sequences of the primers (SEQ ID NOS:3–4) used to amplify the antibody variable domain VH and the CH1 constant domain from the cDNA construct HC-hum-β-glucuronidase.

FIG. 4 shows the ligation of the XbaI/HindIII fragment of vector KS/Fab HC/*E.C.* β-Gluc into vector pTrc 99/FabLC to produce vector pTrc99/dicistr. Fab/*E.c.*β-Gluc.

FIG. 5b and 5c show the organization of vector pTrc99/dicistr. Fab/*E.c.*β-Gluc.

FIG. 5c, 5d, 5e, 5f, 5g, 5h and 5i show the nucleotide and corresponding amino acid sequences (SEQ ID NOS:5–7) for the VK and CK domain coding sequences inserted into the vector pTrc99/dicistr. Fab/*E.c.*β-Gluc.

FIG. 5a–5c shows the nucleotide and corresponding amino acid sequences for the VH, CH1 and *E. coli* β-glucuronidase coding sequences inserted into the vector pTrc99/dicistr. Fab/*E.c.*β-Gluc.

DETAILED DESCRIPTION OF THE PREFERRED EMBODIMENTS

Figure 1B:
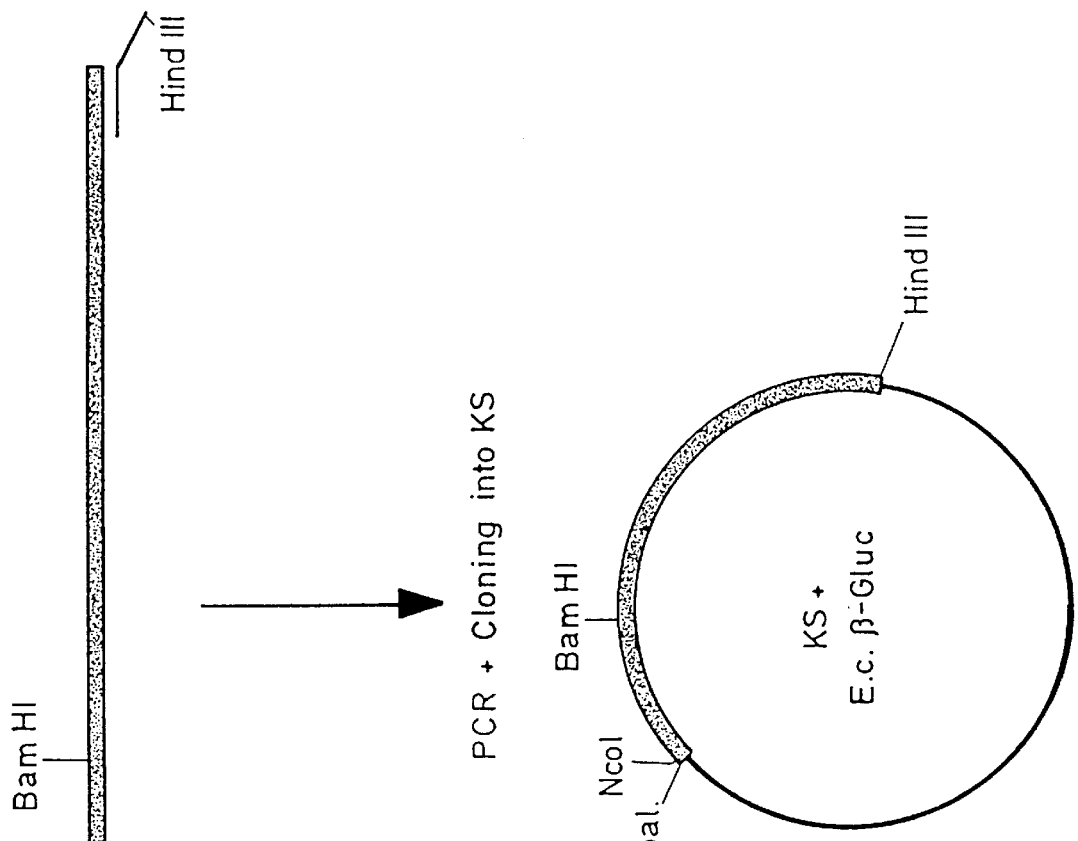

It has now been found that a antibody fragment, such as Mab BW 431/26 (an Fab molecule), Güssow & Seemann, *Methods in Enzymology*, 203:99–121 (1991), or a complete antibody molecule, can be expressed cytoplasmically in a functionally active state, i.e., while retaining its antigen-binding properties in an *E. coli* strain which is deficient in thioredoxin reductase.

Surprisingly, it has furthermore been possible to express an antibody fragment-enzyme fusion molecule composed of, for example, the cytoplasmic, non-disulfide- bridged *E. coli* enzyme β-glucuronidase and, for example, the Fab BW 431/26 which requires intramolecular cystine bridges for correct folding (Fab BW 431/26-*E. coli* β-glucuronidase) in the cytoplasm and to isolate it therefrom in functional form. At the same time, the expressed molecule was soluble and no refolding was necessary to produce a functionally active polypeptide. This opens up novel opportunities for economically producing antibodies, antibody fragments and antibody fragment-enzyme fusion molecule for therapeutic and diagnostic use.

Antibodies and Antibody Fragments

Examples of antibody fragments of the invention include (A) a "half antibody" molecule, i.e., a single heavy:light chain pair, and (B) an antibody fragment, such as the univalent fragments Fab and Fab', the divalent fragment F(ab')$_2$, and a single or double chain Fv fragment. Antibody fragments according to the invention are preferably Fab fragments or antigen-binding regions such as sFv. See Plückthun and Skerra, Meth. Enzymol. 178, pp. 497–515, 1991. Many antibodes are known in the art. Antibodies according to the invention include human antibodies, humanized antibodies, and other antibodies known in the art.

Humanized antibodies are chimeric antibodies comprising non-human and human regions, and have reduced immunoreactivity when used therapeutically in humans. Typically, the variable domains or are of non-human origin and the constant domains are of human origin. Humanized antibodies can also be produced by inserting non-human complimentarity-determining-regions (CDRs) into the framework of a human antibody. An antigen binding site in an antibody is made up of CDRs in the light chain and CDRs in the heavy chain. Humanized antibodies can be produced using recombinant DNA technology well-known in the art. Briefly, oligonucleotides encoding CDRs with desired antigen-recognition properties are used to replace the CDR regions in a human antibody gene. In certain instances, a mouse monoclonal antibody will have the desired antigen-recognition characteristics. These CDR-encoding regions are sequenced and oligonucleotides encoding these regions are inserted into the human antibody gene. See Güssow, Methods in Enzymology 203:99–121 (1991), which describes techniques well known in the art for humanization of antibodies and cloning antibody (immunoglobulin) genes.

The antibodies and antibody fragments according to the invention preferably bind specifically to malignant, cancerous, or tumorigenic cells. It is well known in the art that cancer cells often express specific antigens on their surface, and it is to these antigens that the antibodies and antibody fragments according to the invention specifically bind.

Also illustrative of an antibody fragment within the present invention is a non-peptide "mimetic," i.e., a compound that mimics an epitope binding site of an antibody but that is water-soluble, resistant to proteolysis, and non-immunogenic. Conformationally restricted, cyclic organic peptides which mimic any of these antibodies can be produced in accordance with known methods described, for example, by Saragovi, et al., *Science* 253: 792 (1991).

In accordance with the present invention, antibody fragments within the invention can be obtained from a antibody by methods that include digestion with enzymes such as pepsin or papain and/or cleavage of disulfide bonds by chemical reduction. Alternatively, antibody fragments encompassed by the present invention can be synthesized using an automated peptide synthesizer such as those supplied commercially by Applied Biosystems, Multiple Peptide Systems and others, or they may be produced manually, using techniques well known in the art. See Geysen et al., *J. Immunol. Methods* 102: 259 (1978). Direct determination of the amino acid sequences of the variable regions of the heavy and light chains of the antibodies according to the invention can be carried out using conventional techniques.

As noted, a fragment according to the present invention can be an Fv fragment. An Fv fragment of an antibody is made up of the variable region of the heavy chain (Vh) of an antibody and the variable region of the light chain of an antibody (Vl). Proteolytic cleavage of an antibody can produce double chain Fv fragments in which the Vh and Vl regions remain non-covalently associated and retain antigen binding capacity.

Double chain Fv fragments also can be produced by recombinant expression methods well known in the art. See Plückthun and Skerra, Meth. Enzymol. 178, pp. 497–515 (1991), Skerra et al., *Science* 240: 1038 (1988), and King et al., *Biochemical J.* 290: 723 (1991). Briefly, the amino acid sequence of the variable regions of the heavy and light chains of antibodies known in the art can be obtained by direct amino acid sequencing using methods well known to those in the art. From this amino acid sequence, synthetic genes can be designed which code for these variable regions and they can both be inserted into an expression vector. Alternatively, nucleotide sequences known in the art which encode antibodies can be employed. Two polypeptides can be expressed simultaneously from a mammalian or bacterial host, resulting in formation of an active Fv fragment.

An antibody fragment of the present invention also can be a single-chain molecule or so-called "single chain antigen binding polypeptide," a phrase used in this description to denote a linear polypeptide that binds antigen with specificity and that comprises variable or hypervariable regions from the heavy and light chain chains of an antibody. Single chain antigen binding polypeptides that retain an antigen-binding capacity that is characteristic of the present invention can be produced by conventional methodology. The Vh and Vl regions of the Fv fragment can be covalently joined and stabilized by the insertion of a disulfide bond. See Glockshuber, et al., *Biochemistry* 1362 (1990). Alternatively, the Vh and Vl regions can be joined by the insertion of a peptide linker. A gene encoding the Vh, Vl and peptide linker sequences can be constructed and expressed using a recombinant expression vector. See Colcher, et al., *J. Nat'l Cancer Inst.* 82: 1191 (1990). Amino acid sequences comprising hypervariable regions from the Vh and Vl antibody chains can also be constructed using disulfide bonds or peptide linkers, as described herein.

Fusion Proteins

Fusion proteins can be made in *E. coli* using recombinant DNA techniques that are well-known in the art. See, e.g., CURRENT PROTOCOLS IN MOLECULAR BIOLOGY pp. 16.0.5–16.7.7 (Ausubel, et al., eds. John Wiley & Sons (1996)). Briefly, a fusion protein vector is constructed for insertion into *E. coli*. This vector will generally contain a selectable marker gene sequence, a controllable transcriptional promoter (such as lac, trp or tac), other translational control sequences such as appropriately positioned ribosome-binding site and initiator ATG and one or more polylinker sequences to facilitate insertion of the fusion protein gene in the correct orientation within the vector. This vector will also contain a "carrier sequence" that encodes a carrier protein; this carrier sequence is inserted into the expression vector 5' of the gene to be expressed. The carrier sequence generally encodes a protein that is strongly expressed in *E. coil*. The carrier sequence will provide the necessary signals for proper expression and the expressed protein will contain an N-terminal region encoded by the carrier sequence. The carrier sequence can encode an entire protein, such as β-glucuronidase and β-galactosidase.

A fusion protein according to the invention generally comprises an antibody or antibody fragment as described above and an enzyme. The production of antibodies and antibody fragments according to the invention are described above, as are the methods for isolating nucleic acid sequences that encode such antibodies and antibody fragments. The enzymes of the fusion proteins according to the invention include cytoplasmic enzymes, including *E. coli* cytoplasmic enzymes such as *E. coli* β-glucuronidase. The *E. coli* β-glucuronidase gene (uid A) has been cloned, sequenced, and expressed as a fusion with the *E. coli* lacZ promoter and coding region by Jefferson et al. (PNAS vol. 83, pp. 8447–8451, 1986). The enzyme β-glucuronidase is capable of cleaving β-glucuronides to toxic counterparts. When fused to an antigen-binding polypeptide, an enzyme in a fusion protein according to the invention can cleave a non-toxic compound (known also as a prodrug) into its active, and toxic, form.

A recombinant expression vector encoding a fusion protein according to the invention can be expressed in *E. coli* using transformation and culturing techniques that are well known in the art, using techniques such as those described by Ausubel, supra, pp. 1.8.1–1.8.8 and 16.0.5–16.4.2. Briefly, calcium chloride can be used to transform *E. coli* with foreign DNA. Those of skill in the art will recognize that the following factors can influence the success of the transformation: harvesting bacterial cells during logarithmic growth phase, keeping cells on ice during transformation and avoiding prolonged exposure of cells to calcium chloride. Electroporation is also well-known in the art as an acceptable transformation method for *E. coli*. Those of skill in the art will recognize the need to vary the electric pulse strength and length to optimize transformation and to add sufficient DNA for transformation.

Thioredoxin reductase-deficient *E. coli*

An *E. coli* strain which is deficient in thioredoxin reductase, for example the strain AD 494, can form disulfide bridges in the cytoplasm and thus enzymes which are naturally secretory, for example alkaline phosphatase, can be expressed intracellularly (Derman et al., *Science*, vol. 262. 1744–1747, 1993). As used in this specification, a thioredoxin reductase-deficient *E. coli* strain is one which (1) has TRR activity that is eliminated or greatly reduced compared to the wild type strain and (2) is capable of producing cytoplasmic proteins with disulfide bonds. *E. coli* strains with (1) mutations in the trxB gene (which codes for TRR) and (2) that are capable of producing cytoplasmic proteins with disulfide bonds are included in the present invention.

A TRR-deficient *E. coli* strain can be isolated by selection methods known in the art. For example, it is known that alkaline phosphatase (AP) requires two intrachain disulfide bonds that are required for AP to retain its enzymatic activity. If AP is expressed in *E. coli* without its signal sequence, it remains in the cytoplasm and its disulfide bonds are not formed. Any mutant *E. coli* which produces enzymatically active, cytoplasmic AP is able to create disulfide bonds in the cytoplasm and is hence TRR-deficient. Thus, one assay to select for TRR-deficient strains is as follows. AP can function as a phosphomonoesterase. In *E. coli*, it is known that fructose-1,6-bisphosphatase (fbp) is a cytoplasmic phosphomonoesterase that is required for thg growth of *E. coli* on gluconeogenic carbon sources such as glycerol. If an AP gene (without its signal sequence) that is expressed in an fbp- mutant will cause such a mutant to grow on glycerol, then the AP gene has enzymatic activity and the mutant is capable of creating disulfide bonds. An *E. coli* mutant selected in this way should be TRR-deficient. Jefferson, supra, describes the use of an fbp- mutant to select for mutant *E. coli* that allow for cytoplasmic disulfide bond formation. These fbp- mutants would only grow on glycerol if expression of a signal-sequenceless AP gene was induced with IPTG (isopropyl thio-β-D-galactopyranoside).

A second selection step can also be employed. AP can also perform the phosphoserine dephosphorylation function of the enzyme encoded by the *E. coli* serB gene. This is the final step in serine biosynthesis. Thus, if a deletion is introduced into the serB gene and induction of the signal-sequenceless AP gene restores the *E. coli* to Ser+, this indicates the presence of active cytoplasmic AP and hence the formation of disulfide bonds in the cytoplasm.

Purification of Fusion Proteins

The fusion proteins of the invention can be purified by various techniques well-known in the art. Following culturing of the transformed *E. coli* harboring the fusion protein gene, the cells are typically disrupted, suspended and pelletted to remove cell debris. Fusion protein can be purified from the supernatant. Numerous methods for ion-exchange chromatography and purification according to size are well characterized in the prior art and one of skill in the art could readily select appropriate purification techniques based on the properties of the fusion protein produced according to the invention. See Ausubel, supra, pp. 16.6.1–16.8.14. Affinity chromatography is also a technique well-known in the art. Anti-idiotype affinity chromatography is useful for purification of fusion proteins with an antibody or antibody fragment component. Briefly, the antiidiotypic antibody is ligated to CnBr-activated Sepharose to create the affinity matrix. The fusion-protein-containing supernatant is exposed to the affinity matrix and the fusion protein is eluted, typically using a pH gradient.

The following examples illustrate but do not limit the invention.

EXAMPLE 1

Construction of a dicistronic expression vector without signal sequences

A) Cloning the *E. coli* β-glucuronidase from *E. coli* RR1

The DNA sequence encoding *E. coli* β-glucuronidase was amplified by PCR from the *E. coli* strain RR1 using the primers (SEQ ID NOS:1–2) *E.c.*βGluc. for (AAG CTT TCA TTG TTT GCC TCC CTG CTG CGG) and *E.c.*βGluc. back (TCT AGA CCA TGG TAC GTC CTG TAC AAA CCC CA), and cloned into the vector P bluescript II KS (Stratagene, La Jolla, Calif.) by way of the Xba I and Hind III sites (FIG. 1).

Figure 2B:
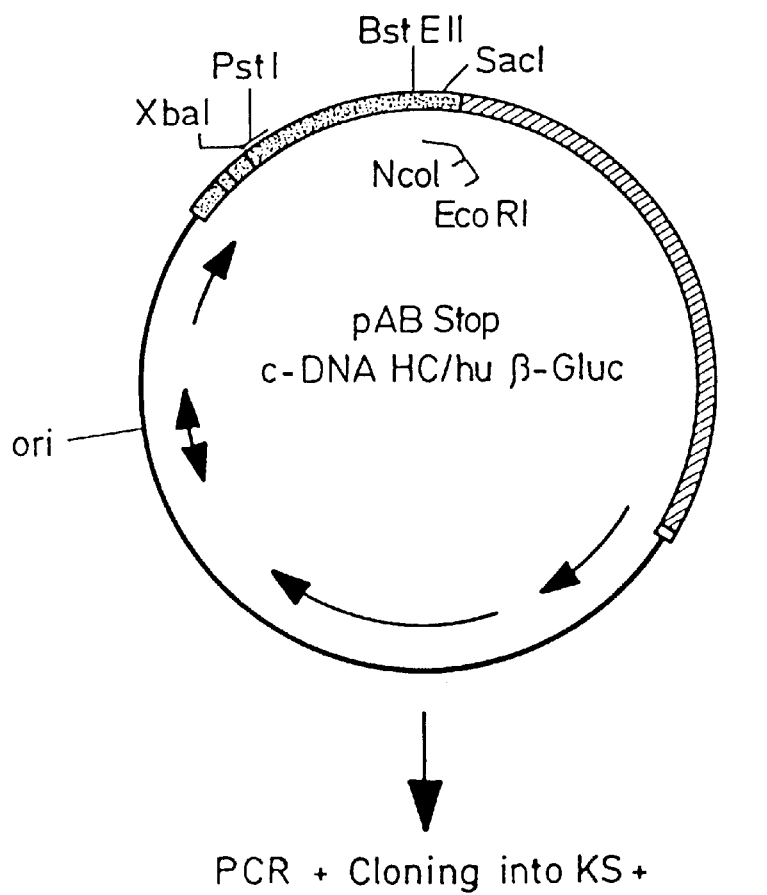
Fig. 2b also shows the cloning of the VH/CH1 region into vector KS by cleavage of the HC-hum-β-glucuronidase using XbaI and EcoRI restriction sites to produce vector KS/Fab HC.
Figure 2B:
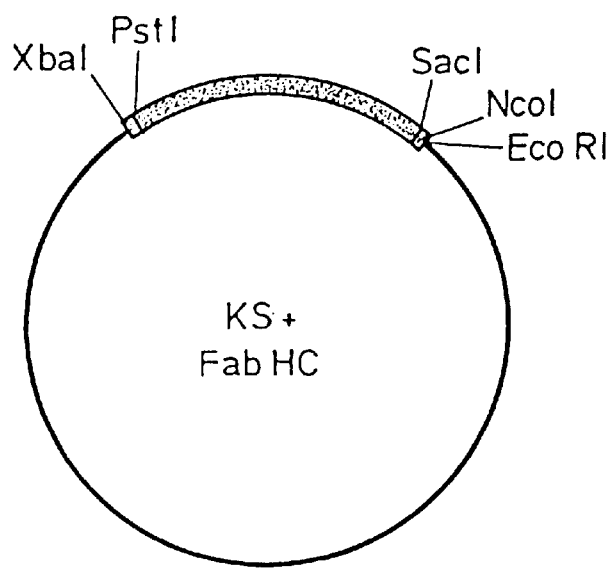

B) Cloning of VH/CH1 and linker Mab BW 431/26 in front of *E. coli* β-glucuronidase The antibody variable domain VH and the constant domain CH1 were amplified by PCR from an HC-human-β-glucuronidase cDNA construct, using the primers (SEQ ID NOS:3–4) Fab HC for (GAA TTC CAT GGA ACC AGA ACC AGA ACC GAG CTC AAC TCT) and Fab HC back (TCT AGA TAA CGA GGG CAA AAA ATG GAG GTC CAA CTG CAG), and cloned into vector p bluescript II KS by way of the Xba I and Eco RI sites (FIG. 2). See Bosslet et al., Br. J, Cancer, 65, 234–238, 1992 and Güssow & Seemann, *Methods in Enzymology*, 203:99–121 (1991). Bosslet describes the construction of the vector comprising a cDNA sequence encoding humanized VH (derived from the VH gene of Mab BW431) and CH1, fused to the gene for human β-glucuronidase that was used in this step. Briefly, the fusion gene comprises the human IgG promoter region and signal peptide exon, the humanized version of the VH gene of Mab BW431 (described in Güssow, supra), and the CH1 exon of human IgG3.

Figure 3:
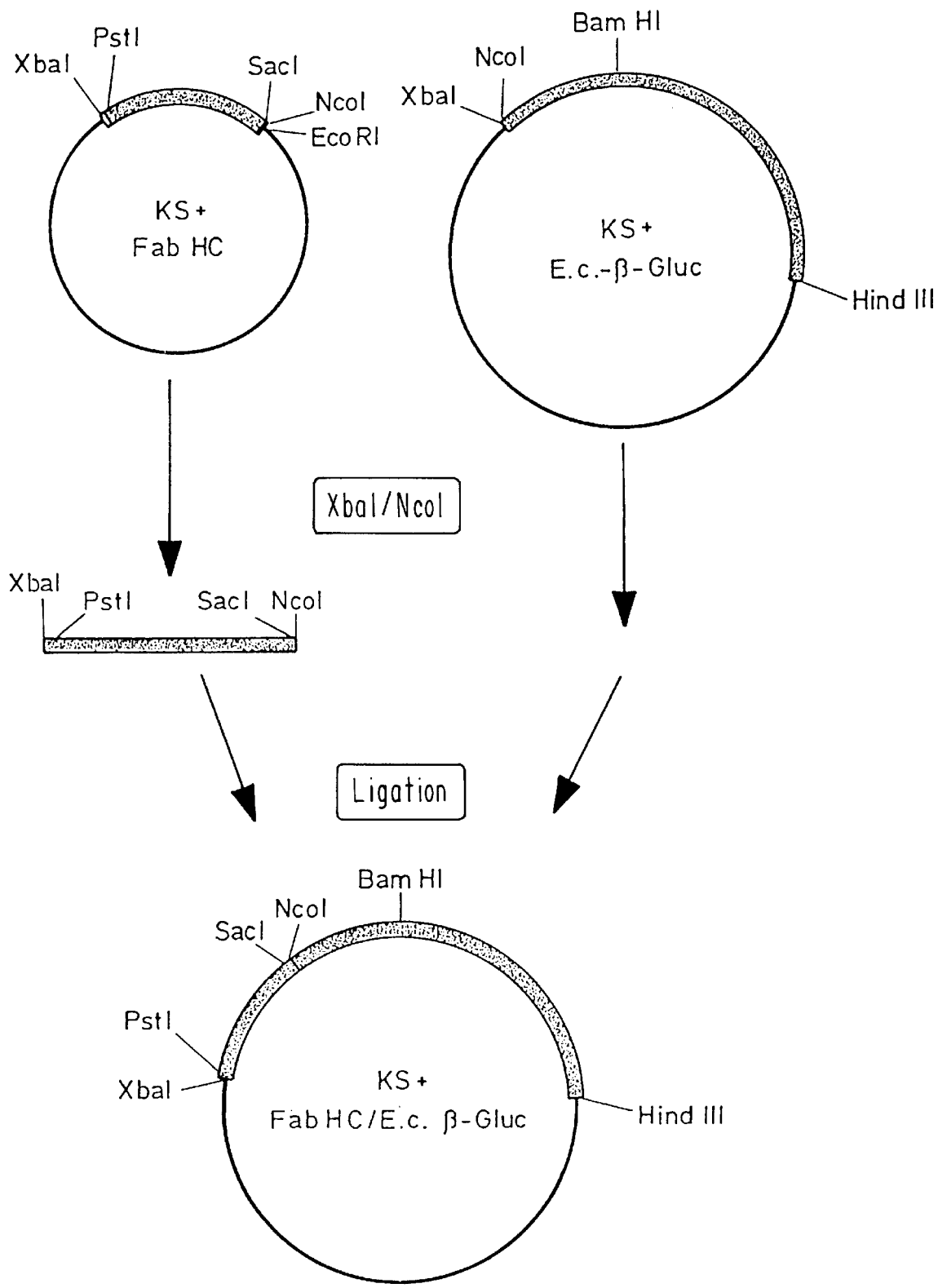
FIG. 3 shows the ligation of the XbaI/NcoI fragment from vector KS/Fab HC into vector KS/A.c.-β-Gluc to produce vector KS/Fab HC/*E.C.* β-Gluc.

After the DNA sequence had been verified, a DNA fragment which was isolated by digesting with XbaI and NcoI was ligated into the vector from cloning step A which had been cut with XbaI and NcoI (FIG. 3).

C) Cloning the Fab BW 431/26—*E. coli* -glucuronidase into pTrc 99

Figure 5A:
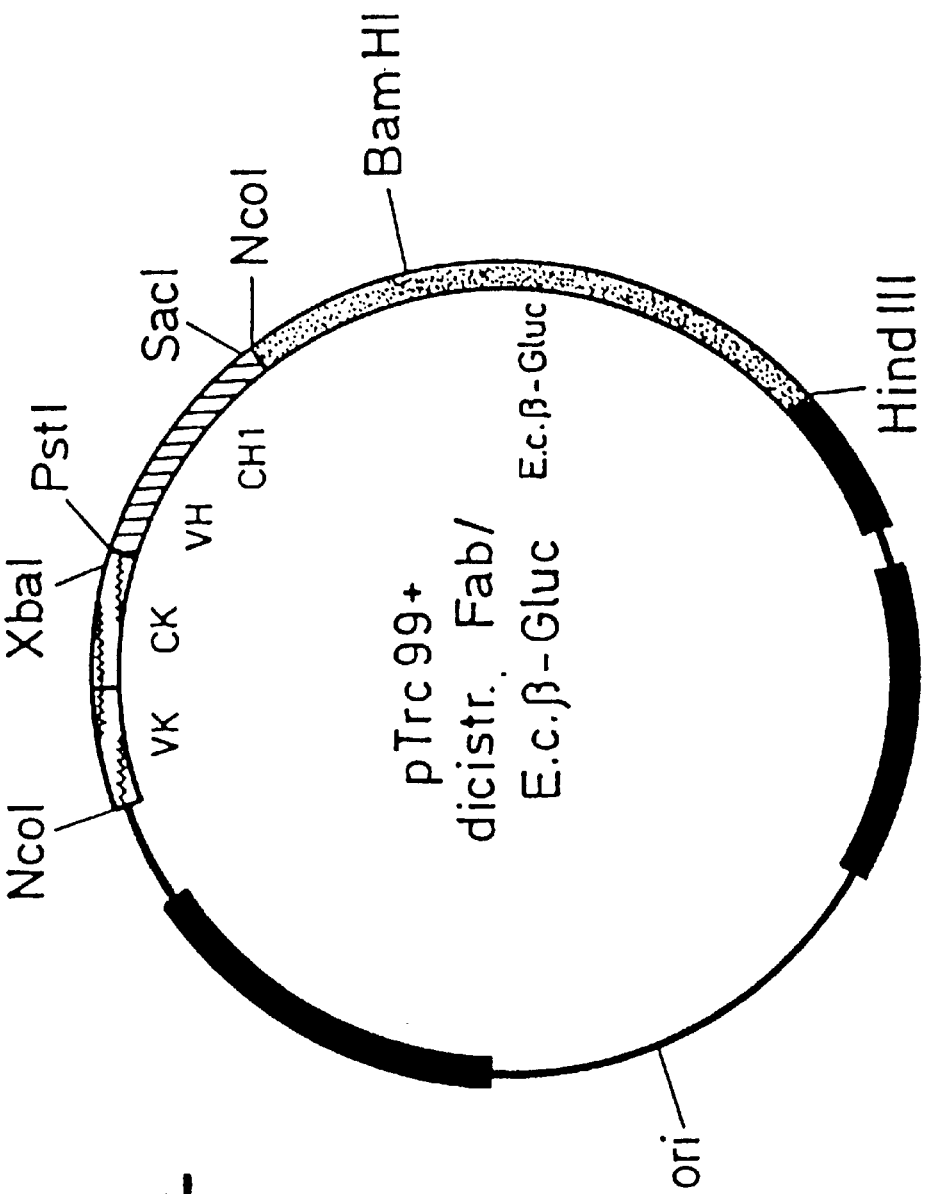

An Xba I/Hind III fragment containing the human heavy chain construct fused to *E. coli* β-glucuronidase was ligated to the light chain of Mab BW 431/26, which was present in the expression vector pTrc99. See Amann et al., Gene 69, 301, 1988 (FIG. 4). The resulting construct has the structure: promotor (trc)—Shine Dalgarno sequence (SD)—VK/CK Mab BW 431/26—SD—VH/CH1 Mab 431/26—*E. coli*-β-gluc.-transcription termination signal (FIG. 5). This construct was used to transform *E. coli* AD 494 using standard transformation techniques known in the art. See, e.g., Ausubel, supra pp. 1.8.1–1.8.8.

EXAMPLE 2

Expression in AD 494

Overnight cultures of AD 494, harboring pTrc dicistr. Fab-*E. coli*-β-gluc., described in Example 1, were diluted 1:10 and incubated at 25° C. until they reached an $OD_{600}$ of 0.7. After inducing with 1 mM IPTG for 19–22 hours, the cells were incubated on ice for 1–1.5 hours. After the cells had been pelletted and resuspended in 10 ml of PBS, pH 7.2, per liter of culture volume, they were disrupted in a French press at 1000–1500 Psi. The disrupted cell suspension was clarified at 20,000 rpm in an SS-34 rotor and the supernatant was employed for the subsequent investigations.

EXAMPLE 3

Purification of the fusion molecule by affinity chromatography.

The disrupted cell suspension supernatant, which had been clarified by passing it through a 2 μm filter, was purified by affinity chromatography. The fusion protein was allowed to bind to an anti-idiotypic monoclonal antibody (BW 2064(34) (6 mg of Mab/ml of CnBr-activated Sepharose 4B) as described in Bosslet, *British J. Cancer* 65:234 (1992) and Bosslett, *British J. Cancer* 63:681 (1991). The fusion protein bound to the affinity column was eluted by pH shifting (pH 7.2–pH 5.0). The peak of antibody was eluted with pH 5.0. (Table 1). The eluate was then concentrated by means of ultrafiltration (Filtron Macrosep. Omega NMWL:30 KD). The cell disruption suspension supernatant, the void volume, the concentrated eluate and the filtrate from the ultrafiltration were analyzed by SDS-PAGE. The band appearing at about 97 KD corresponds, as regards its molecular weight, to the expected fusion protein comprising the heavy chain moiety of the antibody and the E. coli glucuronidase. The band appearing at about 70 KD represents endogenous β-glucuronidase which has been purified concomitantly, during the affinity chromatography, due to the formation of heterotetramers (see below) between expressed heavy chain/β-glucuronidase and endogenous β-glucuronidase.

EXAMPLE 4

TSK 3000 gel chromatography

The native molecule was examined by TSK 3000 gel chromatography and its molecular weight was found to be 450 KD. Since the glucuronidase forms a tetramer in the native state, the observed molecular weight corresponds to that which is to be expected theoretically. This step is described in detail below.

Figure 6:
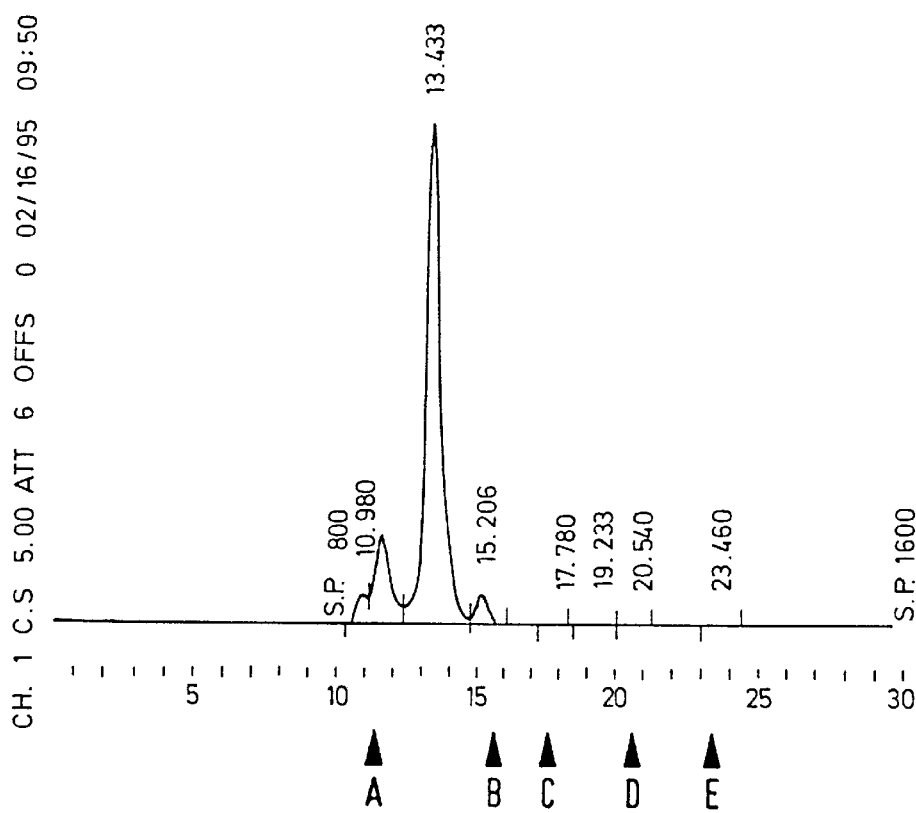
FIG. 6 shows TSK-3000 gel chromatography of a purified fusion protein to determine the molecular weight of the fusion protein. The fusion protein eluted at 13.4 minutes, as evidenced in the peak absorbance at 280 nm. The positions of other molecular weight markers are shown.

400 ng of a fusion protein, which had been purified by anti-idiotype affinity, in 25 µl were chromatographed on a TSK gel G 3000 SW XL column (TOSO HAAS, Cat. No. 3.5W×N3211, 7.8 mm×300 mm) in an appropriate mobile phase (PBS, pH 7.2, 5 g/l maltose, 4.2 g/l arginine) at a flow rate of 0.5 ml/min. The Merck Hitachi HPLC unit (L-400 UV detector, L-6210 intelligent pump, D-2500 chromato-integrator) was operated at about 20 bar, the optical density of the eluate was determined at 280 nm, and 0.5 ml fractions were collected, using an LKB 2111 Multisac fraction collector, and subsequently analyzed in an enzyme activity specificity test (Example 5). The experiment is depicted in FIG. 6. Based on elution pattern of the the molecular weight markers (indicated by arrows), the functionally active Fab-E. coli β-glucuronidase fusion protein was determined to have a molecular weight of about 450 KD.

EXAMPLE 5

Demonstration of the antigen-binding properties and the enzymatic activity

The ability of the Fab-E. coli β-glucuronidase fusion protein to bind specifically to the Mab 431/26-defined epitope on CEA (carcino-embryonic antigen) and simultaneously to exert the enzymic activity of the β-glucuronidase was demonstrated in an enzyme activity specificity test. This assay is carried out as described below:

Polystyrene (96-well) microtiter plates (U shape, Type B, supplied by Nunc, Order No. 4-60445) are incubated with purified CEA (1–5 µg of CEA/ml, 75 µof this per well) or with GIT mucin (same amount as CEA) at R.T. overnight.

The non-adsorbed antigen is removed by aspiration and washed 3× with 0.05 M tris/citrate buffer, pH 7.4.

The microliter plates are left to stand at R.T. with the opening facing downwards on cellulose overnight.

The microtiter plates are incubated with 250 µl of 1% strength casein solution in PBS, pH 7.2, per well (blocking solution) at 20° C. for 30 minutes.

During the blocking, the substrate is made up. The amount of substrate depends on the number of supernatants to be assayed. The substrate is made up fresh for each assay.

Substrate: 4-methylumbelliferyl β-D-glucuronide (Order No.: M-9130 from Sigma), 2.5 mM in 200 mM sodium acetate buffer, pH 5.0, with 0.01% BSA.

The blocking solution is removed by aspiration, and in each case 50 µl of BHK call supernatant which contains the fusion protein are loaded onto the microtiter plate coated with CEA or GIT mucin (that is to say the sample volume required is at least 120 µl).

Incubation at R.T. is then carried out for 30 minutes.

The plates are washed 3× with ELISA washing buffer (Behring, OSEW 96).

The substrate is loaded in (50 µl/wall) and incubated at 37° C. for 2 hours. The plate is covered because of the possibility of evaporation.

After 2 hours, 150 µl of stop solution are pipetted into each well (stop solution =0.2 M glycine +0.2% SDS, pH 11.7).

Evaluation can now be carried out under a UV lamp (excitation energy 380 nm) or in a fluorescence measuring instrument (Fluorosean 11, ICN Biomedicals Cat. No.: 78-611-00).

See also EP-A-0 501 215 A2. The test determines the liberation of 4-methylumbelliferone from 4-methylumbelliferyl-β-glucuronide by the β-glucuronidase moiety of the fusion protein after the fusion protein has bound to the antigen by its Fab moiety. The fluorescence values which were determined are given as relative fluorescence units (FU) (Table 1). This assay demonstrates that the fusion protein elicits significant liberation of methylumbelliferone in the CEA-coated plates.

PEM (polymorphic epithelial mucin)-coated plates served as the control. In these plates, the fluorescence signal was always less than 30 FU.

TABLE 1

|  | 1:2 | 1:4 | 1:8 | 1:16 | 1:32 | 1:64 | 1:128 | 1:256 |
| --- | --- | --- | --- | --- | --- | --- | --- | --- |
| FU, Disrupted cell suspension 1:3 | 8183 | 8149 | 7531 | 6631 | 4560 | 2509 | 1019 | 421.9 |
| FU, void volume 1:1 | 6548 | 5231 | 3222 | 1477 | 525.2 | 214 | 86.19 | 46.29 |
| FU, pH 5.0 eluate 1:3 | 7782 | 7571 | 6360 | 4239 | 1983 | 815.7 | 302 | 113.9 |
| FU, pH 5.0 eluate Ultraconcent. 1:10 | 7904 | 8106 | 8036 | 7153 | 5802 | 3618 | 1651 | 665.7 |
| FU pH 5.0 eluate Ultrafiltrate 1:1 | 74.65 | 172.7 | 90.23 | 52.30 | 38.84 | 25.79 | 23.51 | 19.39 |

What is claimed is:

1. A method for producing a fusion protein comprising an antibody fragment and an enzyme, wherein said antibody fragment is selected from the group consisting of Fv, sFv, Fab, and Fab', said method comprising:
   a) transforming a thioredoxin reductase-deficient *E. coli* strain with a polynucleotide encoding said fusion protein;
   b) culturing said transformed *E. coli* strain to allow for expression of said fusion protein; and
   c) isolating said fusion protein from the cytoplasm of said transformed *E. coli* strain;
   wherein said fusion protein is capable of binding antigen and retains enzymatic activity.

2. A method according to claim 1, wherein said antibody fragment is a fragment of a humanized antibody.

3. A method according to claim 1, wherein said antibody fragment binds specifically to tumor cells.

4. A method according to claim 1, wherein said enzyme is capable of cleaving a nontoxic prodrug to produce a toxic drug.

5. A method according to claim 4, wherein said enzyme is a human cytoplasmic enzyme.

6. A method according to claim 1, wherein said antibody fragment binds specifically to tumor cells and wherein said enzyme is capable of cleaving a nontoxic prodrug to produce a toxic drug.

7. A method according to claim 6, wherein the antibody fragment is a fragment of a humanized antibody and wherein said enzyme is a human cytoplasmic enzyme.

8. A method according to claim 1 wherein said enzyme is *E. coli* β-glucuronidase.

9. A method according to claim 8, wherein said fusion protein is the fusion protein encoded by a vector comprising the nucleotide sequence set forth in SEQ ID NO:5.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Enterobacteriaceae: Escherichia coli (vii) IMMEDIATE SOURCE:
      (B) CLONE: KS + E.c.-Beta-Gluc (xi) SEQUENCE DESCRIPTION: SEQ ID NO: 1:

```
AAGCTTTCAT TGTTTGCCTC CCTGCTGCGG                                    30
```

(2) INFORMATION FOR SEQ ID NO: 2:

(i) SEQUENCE CHARACTERISTICS:
      (A) LENGTH: 32 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Enterobacteriaceae: Escherichia coli (vii) IMMEDIATE SOURCE:
      (B) CLONE: KS + E.c.-Beta-Gluc (xi) SEQUENCE DESCRIPTION: SEQ ID NO: 2:

```
TCTAGACCAT GGTACGTCCT GTACAAACCC CA                                 32
```

(2) INFORMATION FOR SEQ ID NO: 3:

(i) SEQUENCE CHARACTERISTICS:
      (A) LENGTH: 39 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Homo sapiens (vii) IMMEDIATE SOURCE:
      (B) CLONE: pAB Stop c-DNA HC/hu-Beta-Gluc (xi) SEQUENCE DESCRIPTION: SEQ ID NO: 3:

6,008,023

13                                                                                                        14
-continued

```
GAATTCCATG GAACCAGAAC CAGAACCGAG CTCAACTCT                                39
```

(2) INFORMATION FOR SEQ ID NO: 4:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (vii) IMMEDIATE SOURCE:
        (B) CLONE: pAB Stop c-DNA HC/hu-Beta-Gluc (xi) SEQUENCE DESCRIPTION: SEQ ID NO: 4:

```
TCTAGATAAC GAGGGCAAAA AATGGAGGTC CAACTGCAGG AGAGC                         45
```

(2) INFORMATION FOR SEQ ID NO: 5:

(i) SEQUENCE CHARACTERISTICS:
        (A) LENGTH: 3169 base pairs
        (B) TYPE: nucleic acid
        (C) STRANDEDNESS: double
        (D) TOPOLOGY: circular (ii) MOLECULE TYPE: cDNA (iii) HYPOTHETICAL: NO (iv) ANTI-SENSE: NO (vi) ORIGINAL SOURCE:
        (A) ORGANISM: Enterobacteriaceae: Escherichia coli
        (B) STRAIN: pRAJ210

(vii) IMMEDIATE SOURCE:
        (B) CLONE: pTrc99 dicistr. Fab/E.c.-Beta-Gluc (ix) FEATURE:
        (A) NAME/KEY: CDS
        (B) LOCATION:3..641

(ix) FEATURE:
        (A) NAME/KEY: CDS
        (B) LOCATION:666..3162

(xi) SEQUENCE DESCRIPTION: SEQ ID NO: 5:

```
CC ATG GAC ATC CAG ATG ACC CAG AGC CCA AGC AGC CTG AGC GCC AGC           47
   Met Asp Ile Gln Met Thr Gln Ser Pro Ser Ser Leu Ser Ala Ser
    1               5                  10                  15

GTG GGT GAC AGA GTG ACC ATC ACC TGT AGT ACC AGC TCG AGT GTA AGT          95
Val Gly Asp Arg Val Thr Ile Thr Cys Ser Thr Ser Ser Val Ser
                20                  25                  30

TAC ATG CAC TGG TAC CAG CAG AAG CCA GGT AAG GCT CCA AAG CTG CTG         143
Tyr Met His Trp Tyr Gln Gln Lys Pro Gly Lys Ala Pro Lys Leu Leu
             35                  40                  45

ATC TAC AGC ACA TCC AAC CTG GCT TCT GGT GTG CCA AGC AGA TTC AGC         191
Ile Tyr Ser Thr Ser Asn Leu Ala Ser Gly Val Pro Ser Arg Phe Ser
     50                  55                  60

GGT AGC GGT AGC GGT ACC GAC TTC ACC TTC ACC ATC AGC AGC CTC CAG         239
Gly Ser Gly Ser Gly Thr Asp Phe Thr Phe Thr Ile Ser Ser Leu Gln
 65                  70                  75

CCA GAG GAC ATC GCC ACC TAC TAC TGC CAT CAG TGG AGT AGT TAT CCC         287
```

-continued

```
                Pro Glu Asp Ile Ala Thr Tyr Tyr Cys His Gln Trp Ser Ser Tyr Pro
                 80              85                  90                  95

ACG TTC GGC CAA GGG ACC AAG GTG GAA ATC AAA CGT ACT GTG GCT GCA                    335
Thr Phe Gly Gln Gly Thr Lys Val Glu Ile Lys Arg Thr Val Ala Ala
            100                 105                 110

CCA TCT GTC TTC ATC TTC CCG CCA TCT GAT GAG CAG TTG AAA TCT GGA                    383
Pro Ser Val Phe Ile Phe Pro Pro Ser Asp Glu Gln Leu Lys Ser Gly
            115                 120                 125

ACT GCC TCT GTT GTG TGC CTG CTG AAT AAC TTC TAT CCC AGA GAG GCC                    431
Thr Ala Ser Val Val Cys Leu Leu Asn Asn Phe Tyr Pro Arg Glu Ala
        130                 135                 140

AAA GTA CAG TGG AAG GTG GAT AAC GCC CTC CAA TCG GGT AAC TCC CAG                    479
Lys Val Gln Trp Lys Val Asp Asn Ala Leu Gln Ser Gly Asn Ser Gln
        145                 150                 155

GAG AGT GTC ACA GAG CAG GAC AGC AAG GAC AGC ACC TAC AGC CTC AGC                    527
Glu Ser Val Thr Glu Gln Asp Ser Lys Asp Ser Thr Tyr Ser Leu Ser
160                 165                 170                 175

AGC ACC CTG ACG CTG AGC AAA GCA GAC TAC GAG AAA CAC AAA GTC TAC                    575
Ser Thr Leu Thr Leu Ser Lys Ala Asp Tyr Glu Lys His Lys Val Tyr
                180                 185                 190

GCC TGC GAA GTC ACC CAT CAG GGC CTG AGC TCG CCC GTC ACA AAG AGC                    623
Ala Cys Glu Val Thr His Gln Gly Leu Ser Ser Pro Val Thr Lys Ser
                195                 200                 205

TTC AAC AGG GGA GAG TGT TAGTCTAGAT AACGAGGGCA AAAA ATG GAG GTC                     674
Phe Asn Arg Gly Glu Cys                              Met Glu Val
            210                                       1

CAA CTG CAG GAG AGC GGT CCA GGT CTT GTG AGA CCT AGC CAG ACC CTG                    722
Gln Leu Gln Glu Ser Gly Pro Gly Leu Val Arg Pro Ser Gln Thr Leu
    5               10                  15

AGC CTG ACC TGC ACC GTG TCT GGC TTC ACC ATC AGC AGT GGT TAT AGC                    770
Ser Leu Thr Cys Thr Val Ser Gly Phe Thr Ile Ser Ser Gly Tyr Ser
20              25                  30                  35

TGG CAC TGG GTG AGA CAG CCA CCT GGA CGA GGT CTT GAG TGG ATT GGA                    818
Trp His Trp Val Arg Gln Pro Pro Gly Arg Gly Leu Glu Trp Ile Gly
                40                  45                  50

TAC ATA CAG TAC AGT GGT ATC ACT AAC TAC AAC CCC TCT CTC AAA AGT                    866
Tyr Ile Gln Tyr Ser Gly Ile Thr Asn Tyr Asn Pro Ser Leu Lys Ser
        55                  60                  65

AGA GTG ACA ATG CTG GTA GAC ACC AGC AAG AAC CAG TTC AGC CTG AGA                    914
Arg Val Thr Met Leu Val Asp Thr Ser Lys Asn Gln Phe Ser Leu Arg
        70                  75                  80

CTC AGC AGC GTG ACA GCC GCC GAC ACC GCG GTC TAT TAT TGT GCA AGA                    962
Leu Ser Ser Val Thr Ala Ala Asp Thr Ala Val Tyr Tyr Cys Ala Arg
    85                  90                  95

GAA GAC TAT GAT TAC CAC TGG TAC TTC GAT GTC TGG GGT CAA GGC AGC                   1010
Glu Asp Tyr Asp Tyr His Trp Tyr Phe Asp Val Trp Gly Gln Gly Ser
100                 105                 110                 115

CTC GTC ACA GTC ACA GTC TCC TCA GCT TCC ACC AAG GGC CCA TCG GTC                   1058
Leu Val Thr Val Thr Val Ser Ser Ala Ser Thr Lys Gly Pro Ser Val
                120                 125                 130

TTC CCC CTG GCG CCC TGC TCC AGG AGC ACC TCT GGG GGC ACA GCG GCC                   1106
Phe Pro Leu Ala Pro Cys Ser Arg Ser Thr Ser Gly Gly Thr Ala Ala
                135                 140                 145

CTG GGC TGC CTG GTC AAG GAC TAC TTC CCC GAA CCG GTG ACG GTG TCG                   1154
Leu Gly Cys Leu Val Lys Asp Tyr Phe Pro Glu Pro Val Thr Val Ser
            150                 155                 160

TGG AAC TCA GGC GCC CTG ACC AGC GGC GTG CAC ACC TTC CCG GCT GTC                   1202
Trp Asn Ser Gly Ala Leu Thr Ser Gly Val His Thr Phe Pro Ala Val
            165                 170                 175

CTA CAG TCC TCA GGA CTC TAC TCC CTC AGC AGC GTG GTG ACC GTG CCC                   1250
```

```
                Leu Gln Ser Ser Gly Leu Tyr Ser Leu Ser Ser Val Thr Val Pro
                180                 185                 190                 195

TCC AGC AGC TTG GGC ACC CAG ACC TAC ACC TGC AAC GTG AAT CAC AAG         1298
Ser Ser Ser Leu Gly Thr Gln Thr Tyr Thr Cys Asn Val Asn His Lys
                    200                 205                 210

CCC AGC AAC ACC AAG GTG GAC AAG AGA GTT GAG CTC GGT TCT GGT TCT         1346
Pro Ser Asn Thr Lys Val Asp Lys Arg Val Glu Leu Gly Ser Gly Ser
                215                 220                 225

GGT TCC ATG GTA CGT CCT GTA GAA ACC CCA ACC CGT GAA ATC AAA AAA         1394
Gly Ser Met Val Arg Pro Val Glu Thr Pro Thr Arg Glu Ile Lys Lys
            230                 235                 240

CTC GAC GGC CTG TGG GCA TTC AGT CTG GAT CGC GAA AAC TGT GGA ATT         1442
Leu Asp Gly Leu Trp Ala Phe Ser Leu Asp Arg Glu Asn Cys Gly Ile
        245                 250                 255

GAT CAG CGT TGG TGG GAA AGC GCG TTA CAA GAA AGC CGG GCA ATT GCT         1490
Asp Gln Arg Trp Trp Glu Ser Ala Leu Gln Glu Ser Arg Ala Ile Ala
260                 265                 270                 275

GTG CCA GGC AGT TTT AAC GAT CAG TTC GCC GAT GCA GAT ATT CGT AAT         1538
Val Pro Gly Ser Phe Asn Asp Gln Phe Ala Asp Ala Asp Ile Arg Asn
                280                 285                 290

TAT GCG GGC AAC GTC TGG TAT CAG CGC GAA GTC TTT ATA CCG AAA GGT         1586
Tyr Ala Gly Asn Val Trp Tyr Gln Arg Glu Val Phe Ile Pro Lys Gly
            295                 300                 305

TGG GCA GGC CAG CGT ATC GTG CTG CGT TTC GAT GCG GTC ACT CAT TAC         1634
Trp Ala Gly Gln Arg Ile Val Leu Arg Phe Asp Ala Val Thr His Tyr
        310                 315                 320

GGC AAA GTG TGG GTC AAT AAT CAG GAA GTG ATG GAG CAT CAG GGC GGC         1682
Gly Lys Val Trp Val Asn Asn Gln Glu Val Met Glu His Gln Gly Gly
    325                 330                 335

TAT ACG CCA TTT GAA GCC GAT GTC ACG CCG TAT GTT ATT GCC GGG AAA         1730
Tyr Thr Pro Phe Glu Ala Asp Val Thr Pro Tyr Val Ile Ala Gly Lys
340                 345                 350                 355

AGT GTA CGT ATC ACC GTT TGT GTG AAC AAC GAA CTG AAC TGG CAG ACT         1778
Ser Val Arg Ile Thr Val Cys Val Asn Asn Glu Leu Asn Trp Gln Thr
                360                 365                 370

ATC CCG CCG GGA ATG GTG ATT ACC GAC GAA AAC GGC AAG AAA AAG CAG         1826
Ile Pro Pro Gly Met Val Ile Thr Asp Glu Asn Gly Lys Lys Lys Gln
            375                 380                 385

TCT TAC TTC CAT AAT TTC TTT AAC TAT GCC GGG ATC CAT CGC AGC GTA         1874
Ser Tyr Phe His Asn Phe Phe Asn Tyr Ala Gly Ile His Arg Ser Val
        390                 395                 400

ATG CTC TAC ACC ACG CCG AAC ACC TGG GTG GAC GAT ATC ACC GTG GTG         1922
Met Leu Tyr Thr Thr Pro Asn Thr Trp Val Asp Asp Ile Thr Val Val
    405                 410                 415

ACG CAT GTC GCG CAA GAC TGT AAC CAC GCG TCT GTT GAC TGG CAG GTG         1970
Thr His Val Ala Gln Asp Cys Asn His Ala Ser Val Asp Trp Gln Val
420                 425                 430                 435

GTG GCC AAT GGT GAT GTC AGC GTT GAA CTG CGT GAT GCG GAT CAA CAG         2018
Val Ala Asn Gly Asp Val Ser Val Glu Leu Arg Asp Ala Asp Gln Gln
                440                 445                 450

GTG GTT GCA ACT GGA CAA GGC ACT AGC GGG ACT TTG CAA GTG GTG AAT         2066
Val Val Ala Thr Gly Gln Gly Thr Ser Gly Thr Leu Gln Val Val Asn
            455                 460                 465

CCG CAC CTC TGG CAA CCG GGT GAA GGT TAT CTC TAT GAA CTG TGC GTC         2114
Pro His Leu Trp Gln Pro Gly Glu Gly Tyr Leu Tyr Glu Leu Cys Val
        470                 475                 480

ACA GCC AAA AGC CAG ACA GAG TGT GAT ATC TAC CCG CTT CGC GTC GGC         2162
Thr Ala Lys Ser Gln Thr Glu Cys Asp Ile Tyr Pro Leu Arg Val Gly
    485                 490                 495

ATC CGG TCA GTG GCA GTG AAG GGC GAA CAG TTC CTG ATT AAC CAC AAA         2210
```

```
                                              -continued

Ile Arg Ser Val Ala Val Lys Gly Glu Gln Phe Leu Ile Asn His Lys
500                 505                 510                 515

CCG TTC TAC TTT ACT GGC TTT GGT CGT CAT GAA GAT GCG GAC TTA CGT    2258
Pro Phe Tyr Phe Thr Gly Phe Gly Arg His Glu Asp Ala Asp Leu Arg
                    520                 525                 530

GGC AAA GGA TTC GAT AAC GTG CTG ATG GTG CAC GAC CAC GCA TTA ATG    2306
Gly Lys Gly Phe Asp Asn Val Leu Met Val His Asp His Ala Leu Met
                535                 540                 545

GAC TGG ATT GGG GCC AAC TCC TAC CGT ACC TCG CAT TAC CCT TAC GCT    2354
Asp Trp Ile Gly Ala Asn Ser Tyr Arg Thr Ser His Tyr Pro Tyr Ala
            550                 555                 560

GAA GAG ATG CTC GAC TGG GCA GAT GAA CAT GGC ATC GTG GTG ATT GAT    2402
Glu Glu Met Leu Asp Trp Ala Asp Glu His Gly Ile Val Val Ile Asp
565                 570                 575

GAA ACT GCT GCT GTC GGC TTT AAC CTC TCT TTA GGA ATT GGT TTC GAA    2450
Glu Thr Ala Ala Val Gly Phe Asn Leu Ser Leu Gly Ile Gly Phe Glu
580                 585                 590                 595

GCG GGC AAC AAG CCG AAA GAA CTG TAC AGC GAA GAG GCA GTC AAC GGG    2498
Ala Gly Asn Lys Pro Lys Glu Leu Tyr Ser Glu Glu Ala Val Asn Gly
                    600                 605                 610

GAA ACT CAG CAA GCG CAC TTA CAG GCG ATT AAA GAG CTG ATA GCG CGT    2546
Glu Thr Gln Gln Ala His Leu Gln Ala Ile Lys Glu Leu Ile Ala Arg
                615                 620                 625

GAC AAA AAC CAC CCA AGC GTG GTG ATG TGG AGT ATT GCC AAC GAA CCG    2594
Asp Lys Asn His Pro Ser Val Val Met Trp Ser Ile Ala Asn Glu Pro
            630                 635                 640

GAT ACC CGT CCG CAA GGT GCA CGG GAA TAT TTC GCG CCA CTG GCG GAA    2642
Asp Thr Arg Pro Gln Gly Ala Arg Glu Tyr Phe Ala Pro Leu Ala Glu
            645                 650                 655

GCA ACG CGT AAA CTC GAC CCG ACG CGT CCG ATC ACC TGC GTC AAT GTA    2690
Ala Thr Arg Lys Leu Asp Pro Thr Arg Pro Ile Thr Cys Val Asn Val
660                 665                 670                 675

ATG TTC TGC GAC GCT CAC ACC GAT ACC ATC AGC GAT CTC TTT GAT GTG    2738
Met Phe Cys Asp Ala His Thr Asp Thr Ile Ser Asp Leu Phe Asp Val
                680                 685                 690

CTG TGC CTG AAC CGT TAT TAC GGA TGG TAT GTC CAA AGC GGC GAT TTG    2786
Leu Cys Leu Asn Arg Tyr Tyr Gly Trp Tyr Val Gln Ser Gly Asp Leu
                695                 700                 705

GAA ACG GCA GAG AAG GTA CTG GAA AAA GAA CTT CTG GCC TGG CAG GAG    2834
Glu Thr Ala Glu Lys Val Leu Glu Lys Glu Leu Leu Ala Trp Gln Glu
            710                 715                 720

AAA CTG CAT CAG CCG ATT ATC ATC ACC GAA TAC GGC GTG GAT ACG TTA    2882
Lys Leu His Gln Pro Ile Ile Ile Thr Glu Tyr Gly Val Asp Thr Leu
            725                 730                 735

GCC GGG CTG CAC TCA ATG TAC ACC GAC ATG TGG AGT GAA GAG TAT CAG    2930
Ala Gly Leu His Ser Met Tyr Thr Asp Met Trp Ser Glu Glu Tyr Gln
740                 745                 750                 755

TGT GCA TGG CTG GAT ATG TAT CAC CGC GTC TTT GAT CGC GTC AGC GCC    2978
Cys Ala Trp Leu Asp Met Tyr His Arg Val Phe Asp Arg Val Ser Ala
                760                 765                 770

GTC GTC GGT GAA CAG GTA TGG AAT TTC GCC GAT TTT GCG ACC TCG CAA    3026
Val Val Gly Glu Gln Val Trp Asn Phe Ala Asp Phe Ala Thr Ser Gln
                775                 780                 785

GGC ATA TTG CGC GTT GGC GGT AAC AAG AAA GGG ATC TTC ACT CGC GAC    3074
Gly Ile Leu Arg Val Gly Gly Asn Lys Lys Gly Ile Phe Thr Arg Asp
                790                 795                 800

CGC AAA CCG AAG TCG GCG GCT TTT CTG CTG CAA AAA CGC TGG ACT GGC    3122
Arg Lys Pro Lys Ser Ala Ala Phe Leu Leu Gln Lys Arg Trp Thr Gly
805                 810                 815

ATG AAC TTC GGT GAA AAA CCG CAG CAG GGA GGC AAA CAA TGAAGCTT       3169
Met Asn Phe Gly Glu Lys Pro Gln Gln Gly Gly Lys Gln
```

```
Met Asn Phe Gly Glu Lys Pro Gln Gln Gly Lys Gln
820             825             830
```

(2) INFORMATION FOR SEQ ID NO: 6:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Ile Gln Met Thr Gln Ser Pro Ser Ser Leu Ser Ala Ser Val
1               5                   10                  15

Gly Asp Arg Val Thr Ile Thr Cys Ser Thr Ser Ser Val Ser Tyr
            20                  25                  30

Met His Trp Tyr Gln Gln Lys Pro Gly Lys Ala Pro Lys Leu Leu Ile
            35                  40                  45

Tyr Ser Thr Ser Asn Leu Ala Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Trp Ser Ser Tyr Pro Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
        210
```

(2) INFORMATION FOR SEQ ID NO: 7:

(i) SEQUENCE CHARACTERISTICS:
        (A) LENGTH: 832 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Glu Val Gln Leu Gln Glu Ser Gly Pro Gly Leu Val Arg Pro Ser
1               5                   10                  15

Gln Thr Leu Ser Leu Thr Cys Thr Val Ser Gly Phe Thr Ile Ser Ser
            20                  25                  30

Gly Tyr Ser Trp His Trp Val Arg Gln Pro Pro Gly Arg Gly Leu Glu
            35                  40                  45

Trp Ile Gly Tyr Ile Gln Tyr Ser Gly Ile Thr Asn Tyr Asn Pro Ser
        50                  55                  60
```

-continued

```
Leu Lys Ser Arg Val Thr Met Leu Val Asp Thr Ser Lys Asn Gln Phe
 65                  70                  75                  80

Ser Leu Arg Leu Ser Ser Val Thr Ala Ala Asp Thr Ala Val Tyr Tyr
             85                  90                  95

Cys Ala Arg Glu Asp Tyr Asp Tyr His Trp Tyr Phe Asp Val Trp Gly
            100                 105                 110

Gln Gly Ser Leu Val Thr Val Thr Val Ser Ser Ala Ser Thr Lys Gly
        115                 120                 125

Pro Ser Val Phe Pro Leu Ala Pro Cys Ser Arg Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asn His Lys Pro Ser Asn Thr Lys Val Asp Lys Arg Val Glu Leu Gly
    210                 215                 220

Ser Gly Ser Gly Ser Met Val Arg Pro Val Thr Pro Thr Arg Glu
225                 230                 235                 240

Ile Lys Lys Leu Asp Gly Leu Trp Ala Phe Ser Leu Asp Arg Glu Asn
                245                 250                 255

Cys Gly Ile Asp Gln Arg Trp Trp Glu Ser Ala Leu Gln Glu Ser Arg
            260                 265                 270

Ala Ile Ala Val Pro Gly Ser Phe Asn Asp Gln Phe Ala Asp Ala Asp
        275                 280                 285

Ile Arg Asn Tyr Ala Gly Asn Val Trp Tyr Gln Arg Glu Val Phe Ile
    290                 295                 300

Pro Lys Gly Trp Ala Gly Gln Arg Ile Val Leu Arg Phe Asp Ala Val
305                 310                 315                 320

Thr His Tyr Gly Lys Val Trp Val Asn Asn Gln Glu Val Met Glu His
                325                 330                 335

Gln Gly Gly Tyr Thr Pro Phe Glu Ala Asp Val Thr Pro Tyr Val Ile
            340                 345                 350

Ala Gly Lys Ser Val Arg Ile Thr Val Cys Val Asn Asn Glu Leu Asn
        355                 360                 365

Trp Gln Thr Ile Pro Pro Gly Met Val Ile Thr Asp Glu Asn Gly Lys
    370                 375                 380

Lys Lys Gln Ser Tyr Phe His Asn Phe Phe Asn Tyr Ala Gly Ile His
385                 390                 395                 400

Arg Ser Val Met Leu Tyr Thr Thr Pro Asn Thr Trp Val Asp Asp Ile
                405                 410                 415

Thr Val Val Thr His Val Ala Gln Asp Cys Asn His Ala Ser Val Asp
            420                 425                 430

Trp Gln Val Val Ala Asn Gly Asp Val Ser Val Glu Leu Arg Asp Ala
        435                 440                 445

Asp Gln Gln Val Val Ala Thr Gly Gln Gly Thr Ser Gly Thr Leu Gln
    450                 455                 460

Val Val Asn Pro His Leu Trp Gln Pro Gly Glu Gly Tyr Leu Tyr Glu
465                 470                 475                 480

Leu Cys Val Thr Ala Lys Ser Gln Thr Glu Cys Asp Ile Tyr Pro Leu
```

```
                        485                 490                 495
Arg Val Gly Ile Arg Ser Val Ala Val Lys Gly Glu Gln Phe Leu Ile
                500                 505                 510

Asn His Lys Pro Phe Tyr Phe Thr Gly Phe Gly Arg His Glu Asp Ala
                515                 520                 525

Asp Leu Arg Gly Lys Gly Phe Asp Asn Val Leu Met Val His Asp His
                530                 535                 540

Ala Leu Met Asp Trp Ile Gly Ala Asn Ser Tyr Arg Thr Ser His Tyr
545                 550                 555                 560

Pro Tyr Ala Glu Glu Met Leu Asp Trp Ala Asp Glu His Gly Ile Val
                565                 570                 575

Val Ile Asp Glu Thr Ala Ala Val Gly Phe Asn Leu Ser Leu Gly Ile
                580                 585                 590

Gly Phe Glu Ala Gly Asn Lys Pro Lys Glu Leu Tyr Ser Glu Glu Ala
                595                 600                 605

Val Asn Gly Glu Thr Gln Gln Ala His Leu Gln Ala Ile Lys Glu Leu
                610                 615                 620

Ile Ala Arg Asp Lys Asn His Pro Ser Val Val Met Trp Ser Ile Ala
625                 630                 635                 640

Asn Glu Pro Asp Thr Arg Pro Gln Gly Ala Arg Glu Tyr Phe Ala Pro
                645                 650                 655

Leu Ala Glu Ala Thr Arg Lys Leu Asp Pro Thr Arg Pro Ile Thr Cys
                660                 665                 670

Val Asn Val Met Phe Cys Asp Ala His Thr Asp Thr Ile Ser Asp Leu
                675                 680                 685

Phe Asp Val Leu Cys Leu Asn Arg Tyr Tyr Gly Trp Tyr Val Gln Ser
                690                 695                 700

Gly Asp Leu Glu Thr Ala Glu Lys Val Leu Glu Lys Glu Leu Leu Ala
705                 710                 715                 720

Trp Gln Glu Lys Leu His Gln Pro Ile Ile Ile Thr Glu Tyr Gly Val
                725                 730                 735

Asp Thr Leu Ala Gly Leu His Ser Met Tyr Thr Asp Met Trp Ser Glu
                740                 745                 750

Glu Tyr Gln Cys Ala Trp Leu Asp Met Tyr His Arg Val Phe Asp Arg
                755                 760                 765

Val Ser Ala Val Val Gly Glu Gln Val Trp Asn Phe Ala Asp Phe Ala
                770                 775                 780

Thr Ser Gln Gly Ile Leu Arg Val Gly Gly Asn Lys Lys Gly Ile Phe
785                 790                 795                 800

Thr Arg Asp Arg Lys Pro Lys Ser Ala Ala Phe Leu Leu Gln Lys Arg
                805                 810                 815

Trp Thr Gly Met Asn Phe Gly Glu Lys Pro Gln Gln Gly Gly Lys Gln
                820                 825                 830
```